United States Patent [19]
Gharibadeh et al.

[11] Patent Number: 5,458,613
[45] Date of Patent: Oct. 17, 1995

[54] RAPID EXCHANGE TYPE INTRALUMINAL CATHETER WITH GUIDING ELEMENT

[75] Inventors: Ramsin Gharibadeh, San Jose; Susan M. Feltovich, Santa Clara; Estela H. Hilario, Los Altos; Troy L. Thornton, Foster City, all of Calif.

[73] Assignee: Advanced Cardiovascular Systems, Inc., Santa Clara, Calif.

[21] Appl. No.: 388,229

[22] Filed: Feb. 7, 1995

Related U.S. Application Data

[63] Continuation of Ser. No. 92,550, Jul. 15, 1993, abandoned.

[51] Int. Cl.$^6$ ................................................. A61M 29/02
[52] U.S. Cl. ................................................. 606/194; 604/96
[58] Field of Search ........................... 606/191, 192, 606/194, 195, 95–103

[56] References Cited

U.S. PATENT DOCUMENTS

| | | | |
|---|---|---|---|
| 637,103 | 11/1899 | Ewald | 15/435 |
| 4,748,982 | 6/1988 | Horzewski et al. | 606/192 |
| 4,944,745 | 7/1990 | Sogaro et al. | 606/194 |
| 5,135,535 | 8/1992 | Kramer | 606/194 |
| 5,154,725 | 10/1992 | Leopold | 606/194 |
| 5,300,025 | 4/1994 | Wantink | 606/194 |
| 5,300,085 | 4/1994 | Yock | 606/194 |

FOREIGN PATENT DOCUMENTS

WO92/20397  11/1992  WIPO.

*Primary Examiner*—Stephen C. Pellegrino
*Assistant Examiner*—William Lewis
*Attorney, Agent, or Firm*—Crosby, Heafey, Roach & May

[57] ABSTRACT

An intraluminal catheter, particularly a dilatation catheter for PTCA procedures, which is adapted for rapid exchange during an intraluminal procedure and which also allows for the exchange of the guidewire without loss of access to the intraluminal region about the distal end of the catheter. The catheter has a guidewire lumen which extends essentially the length of the catheter. A wall of the catheter shaft which defines at least part of the guidewire lumen has a first slit from the proximal end of the catheter to an area proximal to the second guidewire port and a second slit which extends from the proximal guidewire port to a location spaced proximally from the distal end of the catheter. Also disclosed is an adapter having a slit which is continuous with the slit in the proximal extremity of the catheter shaft which facilitates separation of the guidewire and the catheter when the adapter is fixed to the proximal end of the catheter shaft. A guidewire directing element disposed in the guidewire lumen which has a flexible arm which crosses the guidewire lumen so as to guide a guidewire out the second guidewire port when the guidewire is advanced proximally through the guidewire lumen and which is flexible enough to be pushed aside when a replacement guidewire is advanced distally through the guidewire lumen.

17 Claims, 2 Drawing Sheets

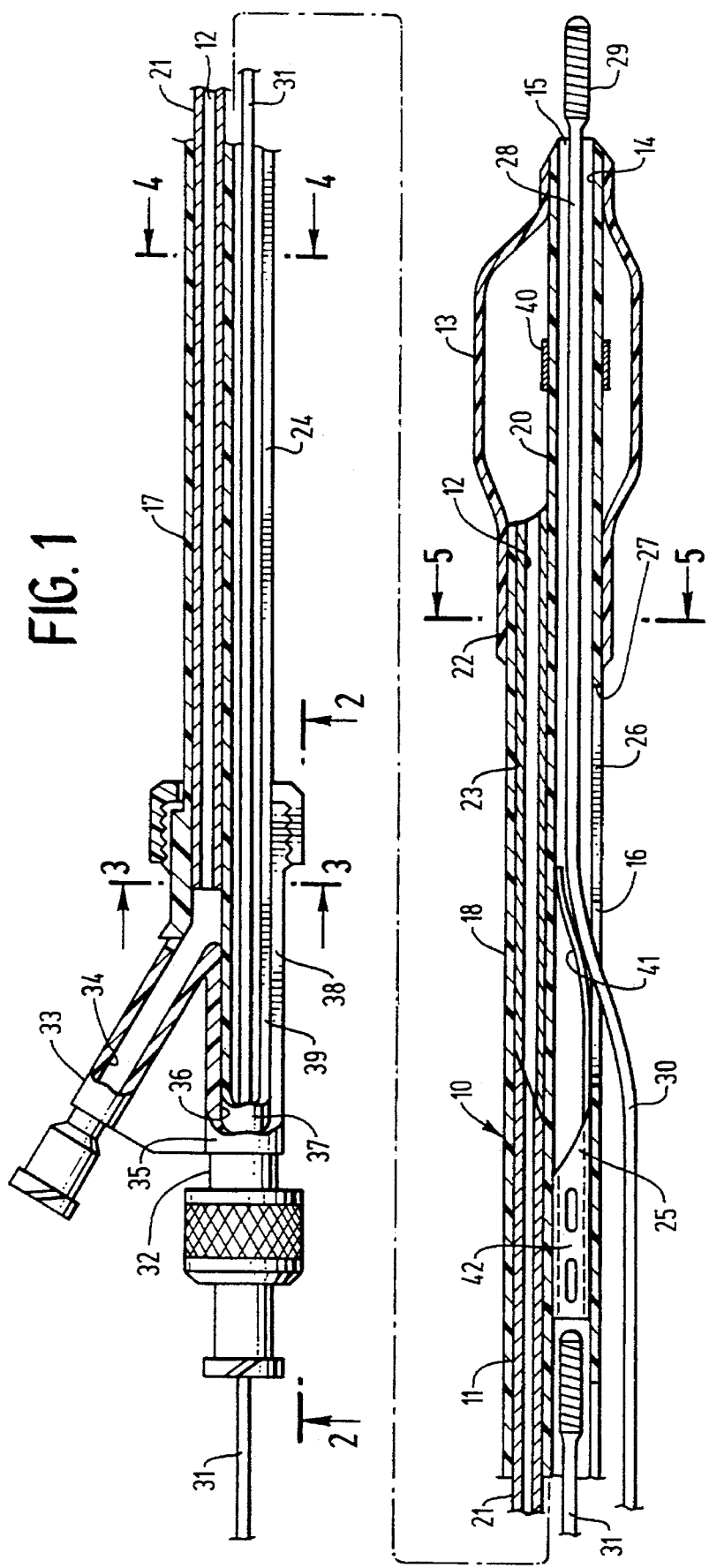

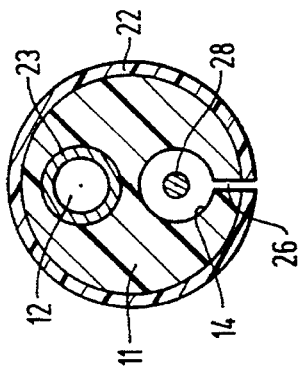
FIG. 5
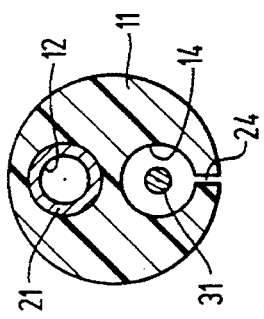
FIG. 4
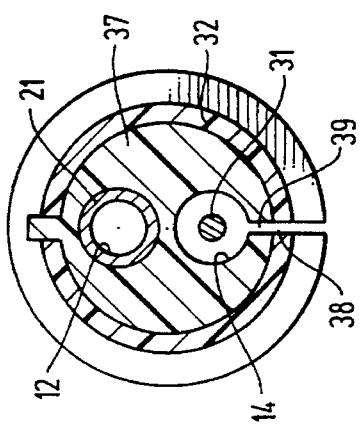
FIG. 3
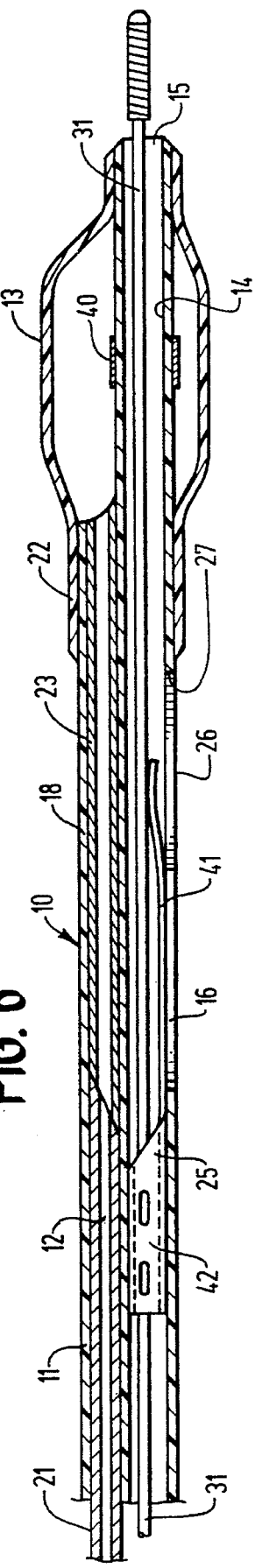
FIG. 6
FIG. 7

RAPID EXCHANGE TYPE INTRALUMINAL CATHETER WITH GUIDING ELEMENT

This is a continuation of application Ser. No. 08/092,550 which was filed on Jul. 15, 1993 now abandoned.

BACKGROUND OF THE INVENTION

This invention generally relates to a rapid exchange type intraluminal catheter system which is suitable for intravascular procedures such as percutaneous transluminal coronary angioplasty (PTCA) and which allows for the exchange of the catheter or the guidewire during such procedures without loss of access to the patient's distal arterial location.

In PTCA procedures, a guiding catheter having a preshaped distal tip is percutaneously introduced into the cardiovascular system of a patient and advanced therein until the preshaped distal tip thereof is disposed within the aorta adjacent to the ostium of the desired coronary artery. The guiding catheter is twisted or torqued from the proximal end to turn the distal tip of the guiding catheter so that it can be guided into the coronary ostium. A dilatation catheter having a balloon on its distal end and a guidewire slidably disposed within an inner lumen of the dilatation catheter are introduced into and advanced through the guiding catheter to its distal tip. The distal tip of the guidewire is usually manually shaped (i.e. curved) before the guidewire is introduced into the guiding catheter along with the dilatation catheter. The guidewire is first advanced out the distal tip of the guiding catheter, into the patient's coronary artery, and torque is applied to the proximal end of the guidewire, which extends out of the patient, to guide the curved or otherwise shaped distal end of the guidewire as the guidewire is advanced within the coronary anatomy until the shaped distal end of the guidewire enters the desired artery. The advancement of the guidewire within the selected artery continues until its distal end crosses the lesion to be dilated. The dilatation catheter is then advanced out of the distal tip of the guiding catheter, over the previously advanced guidewire, until the balloon on the distal extremity of the dilatation catheter is properly positioned across the lesion. Once properly positioned, the dilatation balloon is inflated to a predetermined size with radiopaque liquid at relatively high pressures (e.g., 4–12 atmospheres) to dilate the stenosed region of the diseased artery. The balloon is then deflated so that the dilatation catheter can be removed from the dilated stenosis and blood flow can resume through the dilated artery.

A rapid exchange type dilatation catheter has a short guidewire-receiving sleeve or inner lumen extending a short distance through just the distal portion of the catheter shaft. The sleeve or inner lumen preferably extends proximally at least about 10 cm, typically about 30 cm, from a first guidewire port in the distal end of the catheter to a second guidewire port. A slit may be provided in the catheter wall defining the short guidewire receiving lumen which extends distally from the second guidewire port to a location proximal to the inflatable balloon to facilitate the separation of the catheter from the guidewire. The catheter is advanced within the patient's vascular system with the guidewire disposed within the guidewire receiving inner lumen in the distal section of the catheter shaft in a conventional fashion as previously described. Alternatively, the guidewire may be first advanced within the patient's vasculature until the distal end of the guidewire extends distally to the stenosis to be dilated and then the catheter is mounted onto the proximal end of the in-place guidewire and then advanced over the guidewire until the dilatation balloon is properly disposed across the stenosis. The structure of the catheter allows for the rapid exchange of the catheter without the need for an exchange wire or adding a guidewire extension to the proximal end of the guidewire.

Rapid exchange type catheters are available from the licensee of the present invention, Advanced Cardiovascular Systems, Inc., under the trademark ACS RX® which are basically described and claimed in U.S. Pat. No. 5,061,273 (Yock) and U.S. Pat. No. 4,748,982 (Horzewski et al.).

The catheter design embodying the Yock and Horzewski et al. improvements has been widely praised by members of the medical profession and it has met with much commercial success in the market place. However, there are some inconveniences in its use because the catheter does not allow for the exchange or replacement of the guidewire. For example, the shaped distal tip of the guidewire may become deformed in use or the shape of the distal tip or the size of the guidewire may be found to be no longer suitable for the particular procedure within the patient's vasculature. In this instance the physician might want to remove the guidewire and reshape the distal tip or replace the first guidewire with another having the desired size, stiffness or shape. However, when the guidewire in a dilatation catheter system embodying the Yock and Horzewski et al. improvements is removed, access to the desired distal arterial location through the distal guidewire lumen of the catheter is lost. Unfortunately, there is no way to clinically determine before the guidewire is inserted into the patient in an angioplasty procedure whether a guidewire or a catheter will have to be exchanged during the procedure.

What has been needed and heretofore unavailable is an easily usable intravascular catheter system which allows for the rapid exchange of either the catheter or the guidewire during an intravascular procedure without losing access to the desired distal region of the patient's arterial system. The present invention satisfies this and other needs.

SUMMARY OF THE INVENTION

This invention is directed to a rapid exchange type intraluminal catheter system which allows for the exchange of a guidewire and which can also be used as an over-the-wire type intraluminal catheter without losing access to the location of the distal portion of the catheter within the patient's body lumen.

The catheter system of the invention generally comprises an elongated catheter shaft having proximal and distal ends, a guidewire lumen extending from the proximal end of the catheter shaft to the distal end of the catheter shaft, a first guidewire port in the distal end of the catheter shaft and a second guidewire port spaced a short distance, e.g. from about 10 cm to usually not more than about 50 cm, from the distal end of the catheter shaft, both of said guidewire ports being in communication with the guidewire lumen. A guidewire guiding means is provided within the guidewire lumen to direct the proximal end of a first guidewire being proximally advanced through the guidewire lumen out the second guidewire port, but which allows a second guidewire to be advanced through the guidewire lumen from a location proximal to the guiding means and precludes excursions of the second guidewire out the second guidewire port. A presently preferred guidewire guiding means generally has a support base, preferably tubular, which is adapted to be secured within the guidewire lumen proximal to the second guidewire port and a flexible arm extending distally within the guidewire lumen from the same side of the guidewire lumen in which the second guidewire port is located to the side opposite thereto so as to guide the proximal end of the proximally advancing first guidewire out the second guidewire port. The arm of the guiding means has sufficient flexibility to be pushed aside out of the way when a second guidewire is being advanced distally through the guidewire lumen from a location proximal to the base of the guidewire guiding means.

The flexible arm of the guidewire guiding element, when the guiding element is properly disposed within the guidewire lumen, extends distally from the base of the guiding element and crosses the guidewire lumen inwardly so that a guidewire being advanced proximally through the guidewire lumen will be directed out of the guidewire lumen through the second guidewire port spaced proximally from the distal end of the catheter shaft. The guidewire guiding element, particularly the flexible arm thereof, is preferably formed of a superelastic NiTi alloy which has been thermomechanically treated to provide a relatively large range of strain at relatively high tensile properties. A suitable alloy material consists essentially of about 30 to about 52% titanium and the balance nickel and up to about 10% of one or more additional alloying elements; such additional alloying elements may be selected from the group consisting of iron, cobalt, chromium, platinum, and palladium in amounts up to 3% each and copper and vanadium in amounts of up to 10% each. As used herein all percentages with respect to composition are atomic percent unless noted otherwise. The guiding element is machined from a tubular product which has been formed by cold working at least 10% and heat treating after the cold working at a temperature from about 300° to about 600° C. If needed the tubular product may be straightened before or during the heat treatment. The machined tubular product has a finished martensite-to-austenite transformation temperature of about −25° to about 45° C.

An inflatable member such as a dilatation balloon may be provided on the distal section of the catheter shaft which has an interior in fluid communication with an inflation lumen which extends from the proximal end of the catheter shaft.

To facilitate a catheter exchange during an intravascular procedure, a slit should be provided in a wall of the proximal section of the catheter shaft which defines at least in part the guidewire receiving lumen extending therein. In this manner the catheter shaft can be readily separated from the guidewire disposed within the guidewire lumen. The slit extends from the proximal end of the catheter shaft to a location proximal to the base of the guidewire guiding member disposed within the guidewire lumen. Another slit may be provided in the distal portion of the catheter shaft which extends distally from the second guidewire port to a location spaced proximally from the distal end of the catheter which facilitates separation from a guidewire which is disposed within the guidewire lumen in the distal portion of the catheter and extends out the second guidewire port.

An adapter is provided on the proximal end of the catheter shaft which has an inner lumen for directing a guidewire into the guidewire lumen in the proximal section of the catheter shaft. The adapter is preferably a multi-arm adapter with one arm for directing inflation fluid into the inflation lumen and a second arm which has an inner lumen adapted to direct a guidewire into the guidewire receiving lumen of the catheter shaft. In one presently preferred embodiment, the arm of the adapter which directs a guidewire to the guidewire lumen in the catheter shaft has a slit continuous with the slit in the proximal section of the shaft to facilitate the complete separation of the catheter shaft from a guidewire.

One of the advantageous features of the catheter of the invention is that it can be initially advanced within a patient's vascular system or other body lumen either in a rapid exchange mode with the guidewire extending through just the distal portion of the catheter shaft in the guidewire receiving lumen therein or in a conventional over-the-wire mode with the guidewire extending through the guidewire receiving lumen throughout essentially the entire length of the catheter shaft. The catheter design allows for the exchange of the catheter while the guidewire remains in place or the replacement of the guidewire while the catheter remains in place during an intraluminal procedure such as a PTCA.

To exchange an in-place guidewire during an intraluminal procedure with the catheter system of the invention, the in-place catheter is manually held so as to maintain its position within the patient's vasculature to ensure access to the position therein. The in-place guidewire may then be removed from the guidewire-receiving inner lumen of the catheter and the patient by merely pulling on its proximal end which extends out of the patient. While the in-place guidewire is being removed from the inner lumen of the in-place catheter, the distal end of the in-place catheter is maintained at the desired location within the patient's artery. A replacement guidewire is inserted into the second arm of the adapter and advanced through the guidewire receiving lumen in the proximal and distal sections of the catheter shaft and out the guidewire port in the distal end of the catheter shaft to the desired location within the patient's body lumen. As the replacement guidewire advances through or by the guidewire guiding member, it pushes the flexible arm thereof out of the way, thereby preventing an excursion of the replacement guidewire out the second guidewire lumen. It may be desirable in some instances to have the replacement guidewire already inserted at least into the proximal portion of the guidewire-receiving inner lumen, but proximal to the guidewire guiding means, before the in-place guidewire is removed from the distal portion of the inner lumen so that there is little chance of losing access to the location in the body lumen by the accidental movement of the in-place catheter. When the replacement guidewire is advanced through the in-place catheter and properly positioned in a desired location therein, e.g. across a stenosis in a patient's artery which is to be dilated, the catheter may then be advanced over the replacement guidewire to the desired location so as to perform the desired diagnostic or therapeutic treatment therein.

The intravascular catheter of the invention also allows for the removal and reinsertion of the same guidewire, for example, when the physician wishes to change the shape of the distal end of a guidewire during a procedure. In this operative modality, the in-place guidewire can be withdrawn in essentially the manner described above, the distal tip thereof reshaped and then reintroduced into the in-place catheter, in essentially the same manner as described above, by advancing the guidewire through the adapter on the proximal end of the catheter shaft into the guidewire receiving lumen extending therein and out the first guidewire port in the distal end of the catheter into the patient's coronary anatomy.

To replace the catheter of the invention during a PTCA procedure, the in-place guidewire is manually held so as to maintain its position within the patient's vasculature to ensure access to the position therein, while the in-place dilatation catheter is pulled proximally over the guidewire by the proximal end of the catheter. If the catheter is being used in the rapid exchange mode, the catheter is withdrawn from the patient by peeling the dilatation catheter off of the guidewire through the slit extending distally from the second guidewire port until the distal end of the dilatation catheter exits the proximal end of the guiding catheter, or an adapter attached thereto, at which point the portion of the guidewire exposed distal to the dilatation catheter can be manually held in position while the catheter is removed from the proximal end of the guidewire. If the catheter has been used in an over-the-wire mode, the in-place guidewire exits the second arm of the adapter on the proximal end of the catheter shaft. The catheter is withdrawn from the patient by peeling the dilatation catheter off the guidewire through the slits provided in the adapter and proximal section of the shaft to a location in the shaft proximal to the base of the disposed guidewire guiding element. The remaining distal section (about 10 cm to usually not more than about 50 cm) of the catheter can be removed from the proximal end of the guidewire while manually holding the exposed portion of the guidewire in position.

Once the catheter has been separated from the proximal end of the in-place guidewire, the proximal end of the in-place guidewire is inserted into the guidewire port in the distal end of a replacement catheter having the construction of the present invention. The distal portion of the replacement catheter shaft is advanced distally over the in-place guidewire in the guidewire lumen until the proximal end of the guidewire encounters the flexible arm of the guidewire guiding element which guides the proximal end out the second guidewire port. At this point, the portion of the guidewire which extends out the second guidewire port may be manually held while the replacement catheter in a rapid exchange mode is further advanced into the patient's vasculature over the in-place guidewire to perform the desired intravascular procedure.

As will become more apparent from the following detailed description of the invention, the intraluminal catheter system of the invention allows for a wide variety of intravascular procedures which were heretofore difficult, if not impossible, to perform with a single catheter system. These and other advantages of the invention will become more apparent from the following detailed description of the invention when taken in conjunction with the accompanying exemplary drawings.

BRIEF DESCRIPTION OF THE DRAWINGS

FIG. 1 is an elevational view, partially in section, of a dilatation catheter which embodies features of the invention.

FIG. 2 is a plan view of the proximal end of the catheter shown in FIG. 1 taken along the lines 2—2.

FIG. 3 is a transverse, cross-sectional view of the catheter shown in FIG. 1 taken along the lines 3—3.

FIG. 4 is a transverse, cross-sectional view of the catheter shown in FIG. 1 taken along the lines 4—4.

FIG. 5 is a transverse, cross-sectional view of the catheter shown in FIG. 1 taken along the lines 5—5.

FIG. 6 is a longitudinal cross-sectional view of a distal portion of the catheter shown in FIG. 1 with a guidewire extending through a guidewire lumen from the proximal end of the catheter shaft and out the guidewire port in the distal end of the catheter.

FIG. 7 is a perspective view of the guidewire guiding element shown in FIGS. 1 and 6.

DETAILED DESCRIPTION OF THE INVENTION

FIGS. 1–6 illustrate a rapid exchange type dilatation catheter 10 embodying features of the invention which allows for the exchange of a guidewire while the catheter remains in place within a patient's arterial system so as to avoid loss of the arterial position and also allows for the exchange of the catheter while a guidewire remains in place. The catheter 10 generally comprises an elongated catheter shaft 11, an inflation lumen 12 adapted to direct inflation fluid from the proximal end of the catheter shaft to the interior of an inflatable dilatation balloon 13 on a distal portion of the catheter shaft and a guidewire-receiving inner lumen 14 extending therein from the proximal end of the catheter shaft to a first guidewire port 15 in the distal end of the catheter shaft. A second guidewire port 16, which is also in communication with the guidewire lumen 14, is provided in the wall forming at least in part the catheter shaft 11 at a location a short distance, e.g. 10 to 50 cm from the distal end of the catheter shaft and a substantial distance from the proximal end of the catheter shaft.

As shown in FIGS. 1–5, particularly FIGS. 3–5 the proximal section 17 and the distal section 18 of the catheter shaft 11 are of a dual lumen construction with the inflation lumen 12 and guidewire receiving lumen 14 having circular transverse cross-sections. The inflation lumen 12 terminates at the proximal end of the balloon 13 and is in fluid communication with the interior of the balloon. Tubular extension 20 of the catheter shaft 11, which defines in part the guidewire receiving lumen 14, extends to the distal end thereof. The distal end of the balloon 13 is sealingly secured to the distal end of the extension 20 by suitable means such as heat bonding or an adhesive. The inflation lumen 12 within the proximal section 17 is preferably provided with supporting inner tubular member 21 formed of high strength material such as a polyimide, stainless steel or a suitable superelastic NiTi alloy. The distal part 23 of the supporting inner tubular member 21 may be formed of tubular stock with a thinner wall as shown in FIGS. 1 and 6. The proximal waist 22 of the balloon 13 is secured in a suitable manner, e.g. heat bonding or an adhesive, to the exterior of the distal section 18 of the shaft 11.

The proximal section 17 of the catheter shaft 11 is provided with a proximal slit 24 which extends from the proximal end of the shaft 11 to a location proximal to the guidewire guiding member 25. The distal catheter shaft section 18 is also provided with distal slit 26 which extends from the second or proximal guidewire port 16 to a location 27 proximal to the proximal waist 22 of the balloon 13.

Guidewire 28, which is slidably disposed within inner guidewire lumen 14, has a coil 29 on its distal end which is shown in FIG. 1 extending out the first guidewire port 15 and an elongated core member 30 which is shown extending through the guidewire lumen 14 and out the second guidewire port 16 as would be utilized in a rapid exchange mode. A replacement guidewire 31 is shown within guidewire lumen 14 in the proximal portion of the catheter shaft 11.

A multi-arm adapter 32, which is provided on the proximal end of the catheter shaft 11, has one arm 33 with an inner lumen 34 which is adapted to introduce inflation fluid into the inflation lumen 12 and a second arm 35 with an inner lumen 36 which is adapted to receive a replacement guidewire 31 and guide it into the guidewire receiving lumen 14 within the catheter shaft 11. The proximal end of the catheter shaft 11 is provided with an insert 37 which fits into the interior of the adapter 32 as shown. The second arm 35 of adapter 32 is provided with a slit 38 and the insert 37 is provided with a slit 39, both of the slits being continuous with the slit 24 in the proximal section 17 of the catheter shaft 11. A portion of the insert 37 sealingly connects the inner lumen 34 with the inner inflation lumen 12 within the catheter shaft 11. The insert 37 may be formed as a separate element and then secured to the proximal end of the catheter shaft 11 or formed as part of the catheter shaft as depicted in FIG. 1.

A radiopaque marker 40 is disposed about the tubular extension 20 which extends within the interior of the balloon 13 to facilitate the fluoroscopic observation thereof during an intravascular procedure. A visual marker (not shown) may also be provided on the proximal section 17 of the catheter body 11 to allow the physician to fluoroscopically determine the location of the proximal guidewire port 16 during an intravascular procedure. Other visual markers (not shown) for the brachial and femoral arteries may be provided on the proximal section 17 of the shaft 11 in a conventional fashion.

FIG. 6 depicts the guidewire guiding element 25 with the flexible arm 41 being displaced laterally by the replacement guidewire 31 as it is advanced distally through the guidewire lumen 14.

FIG. 7 illustrates in perspective a guidewire guiding element 25 shown in FIG. 1 which has a tubular base 42 adapted to be tightly fitted or otherwise secured within the guidewire lumen 14 as shown in FIG. 1, and flexible arm 41. The arm 41 is formed so as to extend across the guidewire lumen from a location adjacent to the second guidewire port 16, as shown in FIG. 1, and guide the proximal end of a guidewire 28 which is being advanced proximally through the inner lumen 14 out the second or proximal guidewire port 16. At least the flexible arm 41, preferably the entire element 25, is formed of a superelastic alloy having a final austenite transformation temperature ($A_f$) of less than about 40° C. The preferred alloy is a nickel-titanium containing alloy which preferably contains about 32 to about 52% titanium and the balance nickel and up to 10% additional alloying elements. The additional alloying elements may include iron, cobalt, chromium, platinum and palladium in amounts up to about 3% and cooper and vanadium in amounts up to 10% each. A nickel content exceeding 50% causes brittleness and prevents effective cold marking. The element is formed, e.g. machined, from superelastic tubing having the desired composition and having been processed by cold working from about 10 to about 75% and thermally treating from about 300° to about 600° C. If necessary, the tubular product may be straightened during or prior to the thermal treatment.

The catheter system of the invention can be inserted into the patient in a conventional rapid exchange fashion with the guidewire 28 preloaded within the inner lumen 14 in the distal section 18 and extending proximally out of the proximal guidewire port 16 or it can be inserted in a conventional over-the-wire fashion with the guidewire extending through the entire length of the guidewire lumen 14 and out the second arm 35 of the adapter 32. When it becomes desirable or necessary at any time during the intravascular procedure to remove or replace either the catheter 10 or the guidewire 28 either may be removed by pulling on the proximal end thereof which extends out of the patient while the catheter or guidewire which remains within the patient is held in position in order to maintain access to the desired intravascular location about the distal end of the catheter or guidewire which remains.

If the guidewire 28 is to be removed when in a rapid exchange mode of operation, the catheter 10 is held in place while the guidewire is pulled out of the proximal end of the guiding catheter (not shown) and adapter thereon. In the over-the-wire mode the guidewire will extend out of the proximal end of the arm 35 of the adapter 32. After the guidewire 28 has been removed from the catheter 10, a replacement guidewire 31 may then be inserted through the end of the arm 35 of the adapter 32 into the inner lumen 14 and advanced therein until the guidewire exits the distal guidewire port 15 in the distal end of the catheter body 11 into the patient's coronary artery. Once the replacement guidewire 31 is properly positioned within the patient's artery, e.g. across a stenosis to be dilated, the dilatation catheter 10 may then be further advanced within the artery, if necessary, over the replacement guidewire to the desired location therein to perform the dilatation or other diagnostic or therapeutic procedure.

If the catheter 10 is to be removed and the guidewire 28 exits the proximal port 16 of the catheter, i.e. the catheter is used in the rapid exchange mode, the catheter is withdrawn and separated from the guidewire through the distal slit 26 until a section of the guidewire 28 is exposed distal to the catheter. When the distal end of the catheter 10 is pulled out of the proximal end of the guiding catheter (or the adapter thereon), the exposed portion of the guidewire 28 distal to the distal end of the catheter 10 may be manually gripped to hold it in place and the catheter 10 can then be removed from the proximal end of the guidewire. If the catheter 10 is being used in an over-the-wire mode with the proximal end of the guidewire extending out of the proximal end of the guiding catheter, the guidewire and the catheter are separated while the catheter is being withdrawn from the proximal end of the guiding catheter (or adapter thereon) by separating the catheter from the guidewire or pulling the catheter off the guidewire via the adapter slit 38, the adapter insert slit 39 and the slit 24 in the wall of the proximal section 17 of the shaft 11. The rest of the procedure is essentially the same as that previously described.

When the catheter 10 has been removed, a replacement catheter may be mounted onto the proximal end of the guidewire 30 by inserting the proximal end of the guidewire through distal guidewire port 15 in the distal end of the replacement rapid exchange type catheter and advancing the catheter over the guidewire disposed within a guidewire receiving lumen 14 of the replacement catheter. The guiding means 25 guides the proximal end of the guidewire out the proximal guidewire port 16 in a rapid exchange fashion. The proximal end of the guidewire 30 is held while the replacement catheter is advanced within the patient in a conventional manner as described in Yock or Horzewski et al. which have been incorporated herein.

The catheter body 11 can be formed by conventional techniques, e.g. extruding, from materials already found useful in intravascular catheters such a polyethylene, polyvinyl chloride, polyesters and composite materials. The various components of the catheter can be joined by suitable adhesive such as the acrylonitrile based adhesive sold as Loctite™ 405. Heat shrinking or heat bonding may also be employed where appropriate. A venting means may be provided to remove air from the interior of the balloon before the catheter is inserted into the patient such as described in U.S. Pat. No. 4,638,805 (Powell) and U.S. Pat. No. 4,821,722 (Samson et al.) which have been incorporated herein.

The size of the catheter body 11 and the guidewire-receiving inner lumen 14 thereof to a large extent are determined by the size of the guidewires 28 and 31 to be employed and the size of the artery or other body lumen through which the catheter must pass. Generally, the diameter of the inner lumen 14 is sufficient to accommodate the guidewire and to allow it to be slidably disposed therein. The diameters of guidewires for coronary use can vary from about 0.006 to about 0.035 inch (0.2–0.89 mm) in diameter, and the inner diameter of the guidewire-receiving inner lumen 14 of the catheter 10 should be about 0.001 to about 0.005 inch (0.025–0.127 mm) larger than the diameter of the guidewire. The catheter body 11 is sufficiently long to extend from outside the proximal end of a guiding catheter, which likewise extends out of the patient, to a stenosis to be treated within the patient's vascular system (or other desired location therein), e.g. from about 100 to about 150 cm when a Seldinger approach through the femoral artery is employed to introduce the catheter 10 into the patient's vasculature. The wall forming the catheter must be of sufficient thickness and strength so that it can be pushed over the guidewires 28 and 31 to the desired location within the patient's blood vessel.

While the invention has been described herein in terms of certain presently preferred embodiments directed to balloon dilatation catheters for use in coronary angioplasty procedures, those skilled in the art will recognize that the catheter of the invention may be used in a variety of body lumens. For example, the invention can be utilized in various diagnostic and therapeutic intraluminal catheters. Additionally, the catheter body may be of concentric construction rather than the dual lumen construction shown herein. Other modifications and improvements may be made to the invention without departing from the scope thereof.

What is claimed is:

1. An intraluminal catheter suitable for performing an intraluminal procedure within a patient's body lumen which permits the exchange of a guidewire during the procedure without the loss of access to the location of the distal portion of the catheter within the patient's body lumen, comprising:

a) an elongated catheter shaft having a proximal and distal ends, a guidewire lumen extending through the catheter shaft to the distal end thereof, a first guidewire port in the distal end of the catheter shaft in fluid communication with the guidewire lumen and a second guidewire port in a distal portion of he catheter shaft which is spaced a short distance from the distal end of the catheter shaft and a substantial distance from the proximal end of the catheter shaft and which is in fluid communication with the guidewire lumen in the distal portion of the catheter shaft; and b) a guidewire directing means disposed within the guidewire lumen having a base which is located within the guidewire lumen and a flexible arm which is secured by one end thereof to the base, which extends distally from the base and which crosses the guidewire lumen from a side having therein the second guidewire port to a side opposite thereto so as to form a guideway adapted to urge out the second guidewire port a guidewire which is advanced proximally through the guidewire lumen from the distal end of the catheter shaft, for directing a guidewire advancing proximally through the guidewire lumen out the second guidewire port and which prevents a guidewire advancing distally through the guidewire lumen from passing through the second guidewire port.

2. The catheter of claim 1 wherein at least the flexible arm of the guidewire directing means is formed of a superelastic alloy containing nickel and titanium.

3. The catheter of claim 2 wherein the alloy containing nickel and titanium has an $A_f$ temperature less than 40° C.

4. The catheter of claim 3 wherein the alloy contains 32–52% titanium and the balance nickel and up to about 10% other alloying elements.

5. The catheter of claim 1 wherein a wall of the catheter shaft defining at least in part the guidewire lumen is provided with a slit extending longitudinally from the proximal end of the catheter shaft to a location proximal to the guidewire directing means and transversely through the wall to be in communication with the guidewire lumen.

6. The catheter of claim 1 wherein a wall of the catheter shaft defining at least in part the guidewire inner lumen is provided with a slit extending longitudinally from the proximal guidewire port to a location spaced proximally from the distal end of the catheter and transversely through the wall to be in communication with the guidewire lumen.

7. The catheter of claim 1 wherein an adapter is provided on the proximal end of the catheter shaft which has an arm with an inner lumen which is adapted to receive a guidewire therein and which is in communication with the guidewire lumen of the catheter body.

8. The catheter of claim 7 wherein the arm of the adapter has a slit continuous with the slit in the proximal section of the catheter shaft to facilitate the separation therefrom of a guidewire disposed within the inner lumen of the arm.

9. The catheter of claim 1 wherein the second guidewire port is spaced at least about 10 cm from the distal end of the catheter shaft and a substantial distance from the proximal end of the catheter shaft.

10. A readily exchangeable dilatation catheter suitable for performing an angioplasty procedure within a patient's artery which permits the exchange of a guidewire during an angiolasty procedure without the loss of access to the location of the distal portion of the catheter within the patient's artery, comprising:

a) an elongated catheter shaft having proximal and distal ends, an inflation lumen extending from the proximal end of the catheter shaft to a location in a distal section of the catheter shaft, a guidewire lumen extending through the catheter shaft to the distal end thereof, a first guidewire port in the distal end of the catheter shaft in fluid communication with the guidewire lumen and a second guidewire port in a distal portion of the catheter shaft which is spaced a short distance from the distal end of the catheter shaft and a substantial distance from the proximal end of the catheter shaft and which is in fluid communication with the guidewire lumen in the distal portion of the catheter shaft; and b) an inflatable member on the distal section of the catheter shaft which has an interior in fluid communication with the inflation lumen;

c) an adapter on the proximal end of the catheter shaft having a first arm with an inner lumen which is adapted to direct inflation fluid into the inflation lumen; and d) a guidewire directing means disposed within the guidewire lumen having a tubular base adapted to be secured within a guidewire lumen and a flexible arm which is secured by one end thereof to the tubular base, which extends distally from the tubular base and which crosses the guidewire lumen from a side having therein the second guidewire port to a side opposite thereto so as to form a guideway adapted to urge out the second guidewire port a guidewire which is advanced proximally through the guidewire lumen from the distal end of the catheter shaft, for directing a guidewire advancing proximally through the guidewire lumen out the second guidewire port and which prevents a guidewire advancing distally through the guidewire lumen from passing through the second guidewire port.

11. The dilatation catheter of claim 10 wherein a wall forming at least part of the catheter shaft is provided with a slit extending from the proximal end of the catheter shaft to a location proximal to the guidewire directing means.

12. The dilatation catheter of claim 10 wherein a wall forming at least part of the catheter shaft is provided with a slit extending from the second guidewire port to a location proximal to the inflatable member.

13. The dilatation catheter of claim 10 wherein the adapter on the proximal end of the catheter shaft has a second arm with an inner lumen which is adapted to receive a guidewire therein and which is in communication with the guidewire receiving lumen.

14. The dilatation catheter of claim 13 wherein the second arm of the adapter has a slit continuous with the slit in the proximal section of the shaft to facilitate the separation therefrom of a guidewire disposed within the inner lumen of the second arm.

15. The dilatation catheter of claim 10 wherein the second guidewire port is spaced proximal to the inflatable member.

16. The dilatation catheter of claim 10 wherein the second guidewire port is spaced at least about 10 cm from the distal end of the catheter shaft and a substantial distance from the proximal end of the catheter shaft.

17. The dilatation catheter of claim 10 wherein the inflatable member has an elongated waist.

* * * * *

UNITED STATES PATENT AND TRADEMARK OFFICE
CERTIFICATE OF CORRECTION

PATENT NO. : 5,458,613
DATED : October 17, 1995
INVENTOR(S) : Gharibadeh et al.

It is certified that error appears in the above-indentified patent and that said Letters Patent is hereby corrected as shown below:

Column 9, line 39, after "having" delete "a".

Column 9, line 44, after "of" delete "he" and insert therefor --the--.

Signed and Sealed this

Twelfth Day of March, 1996

Attest:

BRUCE LEHMAN

*Attesting Officer*     *Commissioner of Patents and Trademarks*